(12) United States Patent
Bingham et al.

(10) Patent No.: US 7,592,156 B2
(45) Date of Patent: Sep. 22, 2009

(54) SYNTHETIC DOG/HUMAN CHIMERIC C-C CHEMOKINE RECEPTOR 2B

(75) Inventors: Brendan William Bingham, Newtown, PA (US); Smita Atul Kotnis, Kendall Park, NJ (US); Jeffrey Dale Kennedy, Newtown, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/880,232

(22) Filed: Jul. 20, 2007

(65) Prior Publication Data

US 2008/0038777 A1 Feb. 14, 2008

Related U.S. Application Data

(60) Provisional application No. 60/832,192, filed on Jul. 20, 2006.

(51) Int. Cl.
   *C12P 21/06* (2006.01)
   *C12N 1/20* (2006.01)
   *C12N 15/00* (2006.01)
   *C07H 21/02* (2006.01)

(52) U.S. Cl. .................. 435/69.1; 435/6; 435/252.3; 435/320.1; 536/23.1

(58) Field of Classification Search ................ 435/69.1, 435/320.1, 253.3, 6; 536/23.1
See application file for complete search history.

(56) References Cited

U.S. PATENT DOCUMENTS 6,132,987 A    10/2000   Charo et al.

FOREIGN PATENT DOCUMENTS

JP        09238688      *   9/1997
WO        200162796     *  12/2001

OTHER PUBLICATIONS

Wong, Lu-Min, "Organization And Differential Expression Of The Human . . . ", The Journal Of Biological Chemistry, vol. 272, Jan. 10 Issue, pp. 1038-1045, 1997.
Herrscher, Richard F., "The Immunoglobulin Heavy-Chain Matrix-Associating Regions . . . ", Genes & Development, 9:3067-3082, 1995.
Charo, I.F., "Molecular Cloning and Functional Expression of two Monocyte Chemoattractant Protein . . . ", PNAS USA vol. 91, pp. 2752-2756, Mar. 1994.
Myers, S. J., "Signal Transduction and Ligand Specificity of the Human Monocyte . . . ", J. of Biol. Chem., vol. 270, No. 11, pp. 5786-5792, Mar. 17, 1995.

* cited by examiner

*Primary Examiner*—Maryam Monshipouri
(74) *Attorney, Agent, or Firm*—Potter Anderson & Corroon LLP

(57) ABSTRACT

Disclosed herein are polynucleotides encoding a chimeric C—C chemokine receptor 2B, the encoded polypeptides thereof, and methods of making and using said polynucleotides and polypeptides.

```
       A A G C T T G C C A C C A T G C T G T G C A C G T C T C G T T C T C G G T T T A   Majority
       ----------------+-------------------+-------------------+-------------------+-
                      10                  20                  30                  40
       ----------------+-------------------+-------------------+-------------------+-
  1    A A G C T T G C C A C C A T G C T G A G C A C G T C A C G C T C A C G C T T T A   CCR2B dog-human
  1    - - - - - - - - - - - - - A T G C T G T C C A C A T C T C G T T C T C G G T T T A   hCCR2B ORF T T A G A A A T A C C A A T G A G A G C G G T G A A G A G G T G A C G A C T T T   Majority
       ----------------+-------------------+-------------------+-------------------+-
                      50                  60                  70                  80
       ----------------+-------------------+-------------------+-------------------+-
 41    T T A G A A A C A C C A A T G A G A G C G G G G A A G A G G T G A C G A C T T T   CCR2B dog-human
 29    T C A G A A A T A C C A A C G A G A G C G G T G A A G A A G T C A C C A C C T T   hCCR2B ORF T T T T G A T T A T G A T T A C G G T G C T C C T T G T C A T A A G T T T G G T   Majority
       ----------------+-------------------+-------------------+-------------------+-
                      90                 100                 110                 120
       ----------------+-------------------+-------------------+-------------------+-
 81    C T T T G A T T A C G A C T A C G G G G C G C C T T G C C A C A A G T T T A G T   CCR2B dog-human
 69    T T T T G A T T A T G A T T A C G G T G C T C C C T G T C A T A A A T T T G A C   hCCR2B ORF G T G C G G C A G G T T G G T G C T G G T T T G C T G C C T C C T C T G T A C T   Majority
       ----------------+-------------------+-------------------+-------------------+-
                     130                 140                 150                 160
       ----------------+-------------------+-------------------+-------------------+-
121    G T G C G A C A G G T G G C T G C T G G T T T G C T G C C G C C T C T G T A C A   CCR2B dog-human
109    G T G A A G C A A A T T G G G G C C C A A C T C C T G C C T C C G C T C T A C T   hCCR2B ORF G T C T T G T G T T T A T T T T T G G T T T T G T G G G C A A C A T G C T T G T   Majority
       ----------------+-------------------+-------------------+-------------------+-
                     170                 180                 190                 200
       ----------------+-------------------+-------------------+-------------------+-
161    G T C T T G T C T T T A T T T T C G G G T T T G T G G G A A A C A T G C T T G T   CCR2B dog-human
149    C G C T G G T G T T C A T C T T T G G T T T T G T G G G C A A C A T G C T G G T   hCCR2B ORF T G T G C T G A T T T T G A T C A A C T G T A A G A A G C T G A A G T G C T T G   Majority
       ----------------+-------------------+-------------------+-------------------+-
                     210                 220                 230                 240
       ----------------+-------------------+-------------------+-------------------+-
201    T G T G C T G A T T T T G A T C A A C T G T A A G A A G C T G A A G T C C A T G   CCR2B dog-human
189    C G T C C T C A T C T T A A T A A A C T G C A A A A A G C T G A A G T G C T T G   hCCR2B ORF A C T G A C A T T T A T C T G C T G A A C C T T G C T A T T T C T G A T T T G C   Majority
       ----------------+-------------------+-------------------+-------------------+-
                     250                 260                 270                 280
       ----------------+-------------------+-------------------+-------------------+-
241    A C C G A C A T A T A T C T G C T G A A C C T T G C T A T T T C C G A T T T G C   CCR2B dog-human
229    A C T G A C A T T T A C C T G C T C A A C C T G G C C A T C T C T G A T C T G C   hCCR2B ORF T T T T T C T T C T T A C T C T C C C T T T T T G G G C T C A C T C T G C T G C   Majority
       ----------------+-------------------+-------------------+-------------------+-
                     290                 300                 310                 320
       ----------------+-------------------+-------------------+-------------------+-
281    T T T T T C T C C T G A C G A T C C C T T T T T G G G C C C A C T A T G C C G C   CCR2B dog-human
269    T T T T T C T T A T T A C T C T C C C A T T G T G G G C T C A C T C T G C T G C   hCCR2B ORF T A A T G G G T G G G T G T T T G G G G A T G T T A T G T G C A A G T T C T T C   Majority
       ----------------+-------------------+-------------------+-------------------+-
                     330                 340                 350                 360
       ----------------+-------------------+-------------------+-------------------+-
321    T A A C G G C T G G C T G C T G G G C G A A G T T A T G T G C A A G T C C T T C   CCR2B dog-human
309    A A A T G A G T G G G T C T T T G G G A A T G C A A T G T G C A A A T T A T T C   hCCR2B ORF A C C G G G C T G T A T C A C A T C G G T T A T T T T G G C G G G A T G T T T T   Majority
       ----------------+-------------------+-------------------+-------------------+-
                     370                 380                 390                 400
       ----------------+-------------------+-------------------+-------------------+-
361    A C C G G C C T C T A T C A C A T A G G G T A C T T T G G A G G G A C G T T T T   CCR2B dog-human
349    A C A G G G C T G T A T C A C A T C G G T T A T T T T G G C G G A A T C T T C T   hCCR2B ORF
```

FIG. 1 CONTINUED

```
        T C A T T A T C C T G C T T A C T A T T G A T C G A T A T C T G G C T A T T G T  Majority
        ------------------+-------------------+-------------------+-------------------+-
                        410                 420                 430                 440
        ------------------+-------------------+-------------------+-------------------+-
    401 T C A T T A T A C T G C T T A C T A T T G A T C G A T A T C T G G C A A T A G T  CCR2B dog-human
    389 T C A T C A T C C T C C T G A C A A T C G A T A G A T A C C T G G C T A T T G T  hCCR2B ORF C C A T G C T G T G T T T G C T T T G A A G G C C C G G A C G G T C A C C T T T  Majority
        ------------------+-------------------+-------------------+-------------------+-
                        450                 460                 470                 480
        ------------------+-------------------+-------------------+-------------------+-
    441 C C A C G C C G T C T T C G C G T T G A A G G C C C G G A C C G T C A C A T T C  CCR2B dog-human
    429 C C A T G C T G T G T T T G C T T T A A A A G C C A G G A C G G T C A C C T T T  hCCR2B ORF G G G T G G T T A C T T G T G T G G T T A C C T G G T T G G T T G C T G T G T    Majority
        ------------------+-------------------+-------------------+-------------------+-
                        490                 500                 510                 520
        ------------------+-------------------+-------------------+-------------------+-
    481 G G A G T G G T T A C T T C C G G G G T T A C A T G G A T G G T T G C A G T G T  CCR2B dog-human
    469 G G G G T G G T G A C A A G T G T G A T C A C C T G G T T G G T G G C T G T G T  hCCR2B ORF T T G C T T C T G T C C C C G G A A T C A T C T T T A C T A C T T T C C A G A T  Majority
        ------------------+-------------------+-------------------+-------------------+-
                        530                 540                 550                 560
        ------------------+-------------------+-------------------+-------------------+-
    521 T C G C C T C T C T C C C C G A A T C A T A T T C A C C A C T G T C C A G A T    CCR2B dog-human
    509 T T G C T T C T G T C C C A G G A A T C A T C T T T A C T A A A T G C C A G A A  hCCR2B ORF C G A A G A T T C T T T T T C T T T T T G T G G C C C T T A T T T T C C G C G G  Majority
        ------------------+-------------------+-------------------+-------------------+-
                        570                 580                 590                 600
        ------------------+-------------------+-------------------+-------------------+-
    561 C G A A G A T T C T T T C T C T T C T T G T A G C C C A C A A T T T C A G C A G  CCR2B dog-human
    549 A G A A G A T T C T G T T T A T G T C T G T G G C C C T T A T T T T C C A C G A  hCCR2B ORF G G C T G G A A T A A T T T C C A T A C G A T T A T G C G G A G C G T T T T G G  Majority
        ------------------+-------------------+-------------------+-------------------+-
                        610                 620                 630                 640
        ------------------+-------------------+-------------------+-------------------+-
    601 G C C T G G A A G A A C T T C C A T A C G A T T A T G C G G A G C G T G T T G G  CCR2B dog-human
    589 G G A T G G A A T A A T T T C C A C A C A A T A A T G A G G A A C A T T T T G G  hCCR2B ORF G G C T G G T C C T G C C G C T T T T G G T C A T G G T G A T T T G T T A C T G  Majority
        ------------------+-------------------+-------------------+-------------------+-
                        650                 660                 670                 680
        ------------------+-------------------+-------------------+-------------------+-
    641 G C C T G G T C C T G C C A C T T T T G G T C A T G G T G A T T T G T T A C A G  CCR2B dog-human
    629 G G C T G G T C C T G C C G C T G C T C A T C A T G G T C A T C T G C T A C T C  hCCR2B ORF G G G C A T T C T G A A G A C C C T G C T T C G G T G T C G G A A C G A G A A G  Majority
        ------------------+-------------------+-------------------+-------------------+-
                        690                 700                 710                 720
        ------------------+-------------------+-------------------+-------------------+-
    681 C G C C A T T C T G A A G A C C C T G C T G A G A T G T C G G A A C G A G A A A  CCR2B dog-human
    669 G G G A A T C C T G A A A A C C C T G C T T C G G T G T C G A A A C G A G A A G  hCCR2B ORF A A G A G G C A T A G G G C C G T G A G G G T G A T C T T C G T G A T C A T G A  Majority
        ------------------+-------------------+-------------------+-------------------+-
                        730                 740                 750                 760
        ------------------+-------------------+-------------------+-------------------+-
    721 A A G A G A C A T A A G G C C G T G A A G C T G A T C T T C G T G A T C A T G A  CCR2B dog-human
    709 A A G A G G C A T A G G G C A G T G A G A G T C A T C T T C A C C A T C A T G A  hCCR2B ORF T T G T T T A T T T T T T G T T T T G G G C T C C T T A T A A C A T T G T G C T  Majority
        ------------------+-------------------+-------------------+-------------------+-
                        770                 780                 790                 800
        ------------------+-------------------+-------------------+-------------------+-
    761 T C G T C T A T T T T T T G T T T T G G G C T C C T A A C A A C A T T G T G C T  CCR2B dog-human
    749 T T G T T T A C T T T C T C T T C T G G A C T C C C T A T A A C A T T G T C A T  hCCR2B ORF T C T C C T G A G T A C C T T C C A G G A G T T C T T C G G T G T G T G T A A C  Majority
        ------------------+-------------------+-------------------+-------------------+-
```

FIG. 1 CONTINUED

```
                   810                 820                 830                 840
       ------------+-------------------+-------------------+-------------------+-
  801  G C T C C T G A G T A C C T T C C A G G A G A G C T T C A A T G T A T C C A A C    CCR2B dog-human
  789  T C T C C T G A A C A C C T T C C A G G A A T T C T T C G G C C T G A G T A A C    hCCR2B ORF T G T G A G T G C A C C T G T C A G C T T G A C C A G G T T A T G C A G G T G A    Majority
       ------------+-------------------+-------------------+-------------------+-
                   850                 860                 870                 880
       ------------+-------------------+-------------------+-------------------+-
  841  T G T A A G T C A A C C T C T C A G C T T G A C C A G A T T A T G C A A G T G A    CCR2B dog-human
  829  T G T G A A A G C A C C A G T C A A C T G G A C C A A G C C A C G C A G G T G A    hCCR2B ORF C G G A G A C T C T T G G G A T G A C T C A C T G C T G T G T G A A T C C G A T    Majority
       ------------+-------------------+-------------------+-------------------+-
                   890                 900                 910                 920
       ------------+-------------------+-------------------+-------------------+-
  881  C G G A G A C T C T G G G A A T G A C C C A C T G C T G T G T G A A C C C G A T    CCR2B dog-human
  869  C A G A G A C T C T T G G G A T G A C T C A C T G C T G C A T C A A T C C C A T    hCCR2B ORF T A T C T A T G C C T T C G T T G G G G A G A A G T T C A G A A G G T A T C T G    Majority
       ------------+-------------------+-------------------+-------------------+-
                   930                 940                 950                 960
       ------------+-------------------+-------------------+-------------------+-
  921  T A T C T A C G C A T T C G T C G G G G A A A A A T T C A G A A G A T A C C T G    CCR2B dog-human
  909  C A T C T A T G C C T T C G T T G G G G A G A A G T T C A G A A G G T A T C T C    hCCR2B ORF T C T G T G T T C T T T C G G A A G C A C A T T A C T A A G C G C T T C T G T A    Majority
       ------------+-------------------+-------------------+-------------------+-
                   970                 980                 990                1000
       ------------+-------------------+-------------------+-------------------+-
  961  T C T G T A T T C T T T C G G A A G C A C A T T A C T A A G C G A T T C T G T A    CCR2B dog-human
  949  T C G G T G T T C T T C C G A A A G C A C A T C A C C A A G C G C T T C T G C A    hCCR2B ORF A A C A G T G T C C G G T T T T T T A C A G G G A G A C C G T G G A T G G A G T    Majority
       ------------+-------------------+-------------------+-------------------+-
                  1010                1020                1030                1040
       ------------+-------------------+-------------------+-------------------+-
 1001  A A C A G T G C C C G G T C T T T T A C A G G G A G A C C G T A G A C G G A G T    CCR2B dog-human
  989  A A C A A T G T C C A G T T T T C T A C A G G G A G A C A G T G G A T G G A G T    hCCR2B ORF T A C T T G C A C C A A T A C G C C T T G C A C T G G G G A G C A G G A A G T T    Majority
       ------------+-------------------+-------------------+-------------------+-
                  1050                1060                1070                1080
       ------------+-------------------+-------------------+-------------------+-
 1041  T A C C A G C A C C A A T A C C C C T A G C A C G G G G G A G C A A G A A G T T    CCR2B dog-human
 1029  G A C T T C A A C A A A C A C G C C T T C C A C T G G G G A G C A G G A A G T C    hCCR2B ORF T C G G C T G G T T T G T G A X X X X                                              Majority
       ------------+-------------------+-
                  1090
       ------------+-------------------+-
 1081  T C C G C C G G G C T G T G A A T T C                                              CCR2B dog-human
 1069  T C G G C T G G T T T A T A A                                                      hCCR2B ORF
```

FIG. 2

```
      M L S T S R S R F I R N T N E S G E E V T T F F D Y D Y G A P C H K F S V K Q V  Majority
      ------------------+------------------+------------------+------------------+-
                       10                 20                 30                 40
      ------------------+------------------+------------------+------------------+-
  1   M L S T S R S R F I R N T N E S G E E V T T F F D Y D Y G A P C H K F S V R Q V  CCR2B dog-human
  1   M L S T S R S R F I R N T N E S G E E V T T F F D Y D Y G A P C H K F D V K Q I  hCCR2B ORF G A G L L P P L Y S L V F I F G F V G N M L V V L I L I N C K K L K S L T D I Y  Majority
      ------------------+------------------+------------------+------------------+-
                       50                 60                 70                 80
      ------------------+------------------+------------------+------------------+-
 41   A A G L L P P L Y S L V F I F G F V G N M L V V L I L I N C K K L K S M T D I Y  CCR2B dog-human
 41   G A Q L L P P L Y S L V F I F G F V G N M L V V L I L I N C K K L K C L T D I Y  hCCR2B ORF L L N L A I S D L L F L L T L P L W A H S A A N G W V L G E A M C K L F T G L Y  Majority
      ------------------+------------------+------------------+------------------+-
                       90                100                110                120
      ------------------+------------------+------------------+------------------+-
 81   L L N L A I S D L L F L L T I P F W A H Y A A N G W L L G E V M C K S F T G L Y  CCR2B dog-human
 81   L L N L A I S D L L F L I T L P L W A H S A A N E W V F G N A M C K L F T G L Y  hCCR2B ORF H I G Y F G G I F F I I L L T I D R Y L A I V H A V F A L K A R T V T F G V V T  Majority
      ------------------+------------------+------------------+------------------+-
                      130                140                150                160
      ------------------+------------------+------------------+------------------+-
121   H I G Y F G G T F F I I L L T I D R Y L A I V H A V F A L K A R T V T F G V V T  CCR2B dog-human
121   H I G Y F G G I F P I I L L T I D R Y L A I V H A V F A L K A R T V T F G V V T  hCCR2B ORF S G V T W L V A V F A S V P G I I F T T V Q I E D S V S V C G P Q F Q Q G W N N  Majority
      ------------------+------------------+------------------+------------------+-
                      170                180                190                200
      ------------------+------------------+------------------+------------------+-
161   S G V T W M V A V F A S L P R I I F T T V Q I E D S F S S C S P Q F Q Q A W K N  CCR2B dog-human
161   S V I T W L V A V F A S V P G I I F T K C Q K E D S V Y V C G P Y F P R G W N N  hCCR2B ORF F H T I M R S V L G L V L P L L V M V I C Y S G I L K T L L R C R N E K K R H K  Majority
      ------------------+------------------+------------------+------------------+-
                      210                220                230                240
      ------------------+------------------+------------------+------------------+-
201   F H T I M R S V L G L V L P L L V M V I C Y S A I L K T L L R C R N E K K R H K  CCR2B dog-human
201   F H T I M R N I L G L V L P L L I M V I C Y S G I L K T L L R C R N E K K R H R  hCCR2B ORF A V K V I F V I M I V Y F L F W A P N N I V L L L S T F Q E S F G V S N C E S T  Majority
      ------------------+------------------+------------------+------------------+-
                      250                260                270                280
      ------------------+------------------+------------------+------------------+-
241   A V K L I F V I M I V Y F L F W A P N N I V L L L S T F Q E S F N V S N C K S T  CCR2B dog-human
241   A V R V I F T I M I V Y F L F W T P Y N I V I L L N T F Q E F F G L S N C E S T  hCCR2B ORF S Q L D Q A T Q V T E T L G M T H C C V N P I I Y A F V G E K F R R Y L S V F F  Majority
      ------------------+------------------+------------------+------------------+-
                      290                300                310                320
      ------------------+------------------+------------------+------------------+-
281   S Q L D Q I M Q V T E T L G M T H C C V N P I I Y A F V G E K F R R Y L S V F F  CCR2B dog-human
281   S Q L D Q A T Q V T E T L G M T H C C I N P I I Y A F V G E K F R R Y L S V F F  hCCR2B ORF R K H I T K R F C K Q C P V F Y R E T V D G V T S T N T P S T G E Q E V S A G L  Majority
      ------------------+------------------+------------------+------------------+-
                      330                340                350                360
      ------------------+------------------+------------------+------------------+-
321   R K H I T K R F C K Q C P V F Y R E T V D G V T S T N T P S T G E Q E V S A G L  CCR2B dog-human
321   R K H I T K R F C K Q C P V F Y R E T V D G V T S T N T P S T G E Q E V S A G L  hCCR2B ORF
```

SYNTHETIC DOG/HUMAN CHIMERIC C-C CHEMOKINE RECEPTOR 2B

CROSS-REFERENCE TO RELATED APPLICATION

This application claims priority from provisional U.S. Patent Application No. 60/832,192, filed Jul. 20, 2006, which is incorporated by reference herein in its entirety.

FIELD OF THE INVENTION

Disclosed herein are novel chimeric C—C chemokine receptor 2B nucleic acids, proteins, vectors, and methods of use thereof.

BACKGROUND OF THE INVENTION

Chemokines and their receptors play a large role in mediating inflammatory responses to injury and disease. Monocyte chemoattractant protein-1 (MCP-1) is a chemokine that, through activation of its cognate receptor, the GPCR C—C chemokine receptor 2 (CCR2), has been implicated in the induction and maintenance of chronic pain. A six amino acid domain within the N-terminal domain of CCR2 binds MCP-1 with high affinity. Once bound, MCP-1 serves as a tethered ligand, and receptor signaling is mediated by secondary points of contact between the ligand and receptor, likely in the extracellular loop and transmembrane domain region of the receptor.

Toward an understanding of MCP-1 and CCR2 binding and signaling, Applicants synthesized and expressed a chimeric dog-human CCR2B molecule that has an overall 85% identity to human CCR2B. Positions 1-35 (N-terminal domain) and 301-360 (TM7 and C-terminal domain) of the chimeric receptor are equivalent to the human residues, while the intervening 265 residues are equivalent to the dog residues. Due to the relatedness between dog and human CCR2B, 211 of these 265 residues are identical between human and dog CCR2B, with the greatest number of mismatches mapping to EC2 and EC3.

SUMMARY OF THE INVENTION

One aspect is directed to novel chimeric C—C chemokine receptor 2B (CCR2B) nucleic acids, proteins, and vectors, as well as uses for same.

Another aspect is for an isolated polynucleotide comprising a nucleotide sequence selected from the group consisting of (a) a nucleotide sequence encoding a chimeric CCR2B polypeptide having at least 86% identity with the amino acid sequence set forth in SEQ ID NO:2; (b) a nucleotide sequence encoding a chimeric CCR2B polypeptide having at least 71% identity with nucleotides 13-1092 of SEQ ID NO:1; (c) a nucleotide sequence which hybridizes with (a) or (b) under the following conditions: 6×SSC at 45° C. and washed at least once with 0.2×SSC, 0.1% SDS at 50° C.; and (d) a nucleotide sequence complementary to (a) or (b).

A further aspect is for an isolated polynucleotide fragment comprising at least 15 contiguous nucleotides from nucleotides 13-1092 of SEQ ID NO:1, wherein the fragment is selected from the group consisting of (a) a fragment containing at least a portion of the sequence of nucleotides 13-117 of SEQ ID NO:1 contiguous with at least a portion of the sequence of nucleotides 118-912 of SEQ ID NO:1; (b) a fragment containing at least a portion of the sequence of nucleotides 118-912 of SEQ ID NO:1 contiguous with at least a portion of the sequence of nucleotides 913-1092 of SEQ ID NO:1; and (c) a fragment containing at least a portion of the sequence of nucleotides 13-117 of SEQ ID NO:1 contiguous with the entire sequence of nucleotides 118-912 of SEQ ID NO:1 contiguous with at least a portion of the sequence of nucleotides 913-1092 of SEQ ID NO:1.

An additional aspect relates to an isolated chimeric CCR2B polypeptide encoded by a nucleotide sequence selected from the group consisting of (a) a nucleotide sequence encoding an amino acid sequence having at least 86% identity with the amino acid sequence set forth in SEQ ID NO:2; and (b) a nucleotide sequence that hybridizes with the complement of the nucleotide sequence of (a) under the following conditions: 6×SSC at 45° C. and washed at least once with 0.2×SSC, 0.1% SDS at 50° C.

Another aspect is for an isolated polypeptide fragment comprising at least 15 contiguous amino acids from SEQ ID NO:2, wherein the fragment is selected from the group of consisting of (a) a fragment containing at least a portion of the sequence of amino acids 1-35 of SEQ ID NO:2 contiguous with at least a portion of the sequence of amino acids 36-300 of SEQ ID NO:2; (b) a fragment containing at least a portion of the sequence of amino acids 36-300 of SEQ ID NO:2 contiguous with at least a portion of the sequence of amino acids 301-360 of SEQ ID NO:2; and (c) a fragment containing at least a portion of the sequence of amino acids 1-35 of SEQ ID NO:2 contiguous with the entire sequence of amino acids 36-300 of SEQ ID NO:2 contiguous with at least a portion of the sequence of amino acids 301-360 of SEQ ID NO:2.

A further aspect is for a method of producing a chimeric CCR2B polypeptide comprising (a) culturing a transformed host cell comprising an expression vector comprising an isolated polynucleotide selected from the group consisting of (i) a nucleotide sequence encoding an amino acid sequence having at least 86% identity with the amino acid sequence set forth in SEQ ID NO:2; (ii) a nucleotide sequence having at least 71% identity with nucleotides 13-1092 of SEQ ID NO:1; (iii) a nucleotide sequence which hybridizes with (i) or (ii) under the following conditions: 6×SSC at 45° C. and washed at least once with 0.2×SSC, 0.1% SDS at 50° C.; and (iv) a nucleotide sequence complementary to (i), (ii), or (iii) in a suitable medium such that a chimeric CCR2B polypeptide is produced; and (b) optionally recovering the chimeric CCR2B polypeptide of step (a).

Other objects and advantages of the present invention will become apparent to those skilled in the art upon reference to the detailed description that hereinafter follows.

BRIEF DESCRIPTION OF THE FIGURES

FIG. 1 is a DNA alignment of dog-human chimeric CCR2B versus wild-type human CCR2B.

FIG. 2 is an amino acid alignment of dog-human chimeric CCR2B versus wild-type human CCR2B.

BRIEF DESCRIPTION OF SEQUENCES

Figure 3:
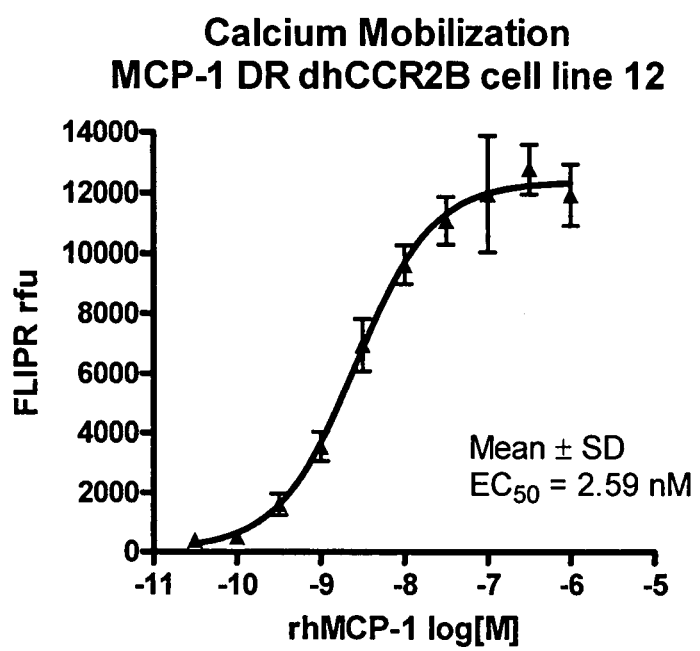
FIG. 3 is a FLIPR assay of calcium mobilization showing human MCP-1 dose dependent stimulation of CHO-K1 cells expressing the chimeric dog-human CCR2B.

SEQ ID NO:1 is a DNA sequence of chimeric CCR2B (coding sequence is bases 13-1092).

SEQ ID NO:2 is an amino acid sequence of dog-human CCR2B chimeric molecule.

DETAILED DESCRIPTION OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning: A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); U.S. Pat. No. 4,683,195; Nucleic Acid Hybridization (B. D. Hames & S. J. Higgins eds. 1984); Transcription and Translation (B. D. Hames & S. J. Higgins eds. 1984); Culture of Animal Cells (R. I. Freshney, Alan R. Liss, Inc., 1987); Immobilized Cells and Enzymes (IRL Press, 1986); B. Perbal, A Practical Guide to Molecular Cloning (1984); Methods in Enzymology (Academic Press, Inc., N.Y.); Gene Transfer Vectors for Mammalian Cells (J. H. Miller and M. P. Calos eds., 1987, Cold Spring Harbor Laboratory); Methods in Enzymology, Vols. 154 and 155 (Wu et al. eds.), Immunochemical Methods in Cell and Molecular Biology (Mayer and Walker, eds., Academic Press, London, 1987); Handbook of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The synthetic CCR2B sequence disclosed herein encodes a functional receptor, as evidenced by Applicants' activation of the receptor (encoded by SEQ ID NO:1) by the CCR2B cognate ligand, monocyte chemoattractant protein-1 (MCP-1, see Example 2). The synthetic sequence encoding the chimeric CCR2B preferentially incorporates a codon-optimized sequence resulting in many (mostly third position) nucleotide changes compared to known CCR2B molecules. For example, the chimeric construct of SEQ ID NO:1 has a 70.4% nucleotide identity to the wild-type human CCR2B (see FIG. 1).

The amino acid composition of the expressed receptor differs in sequence from any known CCR2B receptor. For example, in SEQ ID NO:2, residues 1-35 and 301-360 are human. Residues 36-300 are dog, but, owing to the similarity in sequence between the dog and human orthologues, there are 54 non-identical residues between the dog-human chimera and the wild-type human CCR2B sequence. Thus, the SEQ ID NO:2 chimera has an 85% amino acid identity to the wild-type human CCR2B (see FIG. 2).

I. Definitions

In the context of this disclosure, a number of terms shall be utilized.

The term "cDNA" includes complementary DNA, that is mRNA molecules present in a cell or organism made into cDNA with an enzyme such as reverse transcriptase. A "cDNA library" includes a collection of mRNA molecules present in a cell or organism, converted into cDNA molecules with the enzyme reverse transcriptase, then inserted into vectors. The library can then be probed for the specific cDNA (and thus mRNA) of interest.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

The terms "C—C chemokine receptor 2B" and "CCR2B" refer one of the two receptors ("A" and "B") encoded by the alternatively spliced CCR2 gene (also called the MCP-1 receptor gene), as described in Wong L M et al., J. Biol. Chem. 272:103845 (1997). The terms "chimeric C—C chemokine receptor 2B" and "chimeric CCR2B" refer to CCR2B receptor proteins encoded by a gene constructed from CCR2-encoding sequences taken from multiple species.

As used herein, the term "expression" includes the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook, J., Fritsh, E. F., and Maniatis, T., Molecular Cloning: A Laboratory Manual, 2nd ed., Cold Spring Harbor Laboratory, Cold Spring Harbor Laboratory Press, Cold Spring Harbor, N.Y., 1989). Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general.

The term "expression construct" means any double-stranded DNA or double-stranded RNA designed to transcribe an RNA, e.g., a construct that contains at lease one promoter operably linked to a downstream gene or coding region of interest (e.g., a cDNA or genomic DNA fragment that encodes a protein, or any RNA of interest). Transfection or transformation of the expression construct into a recipient cell allows the cell to express RNA or protein encoded by the expression construct. An expression construct may be a genetically engineered plasmid, virus, or an artificial chromosome derived from, for example, a bacteriophage, adenovirus, retrovirus, poxvirus, or herpesvirus, or further embodiments described under "expression vector" below. An expression construct can be replicated in a living cell, or it can be made synthetically. For purposes of this application, the terms "expression construct", "expression vector", "vector", and "plasmid" are used interchangeably to demonstrate the application of the invention in a general, illustrative sense, and are not intended to limit the invention to a particular type of expression construct. Further, the term expression construct or vector is intended to also include instances wherein the cell utilized for the assay already endogenously comprises such DNA sequence.

A "gene" includes a polynucleotide containing at least one open reading frame that is capable of encoding a particular polypeptide or protein after being transcribed and translated.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operably associated with a different gene than the one it is operably associated with in nature.

The term "homologous" as used herein refers to the sequence similarity between two polymeric molecules, e.g., between two nucleic acid molecules, e.g., two DNA molecules or two RNA molecules, or between two polypeptide molecules. When a nucleotide or amino acid position in both of the two molecules is occupied by the same monomeric nucleotide or amino acid, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'ATTGCC3' and 5'TATGCG3' share 50% homology. By the term "substantially homologous" as used herein, is meant DNA or RNA which is about 50% homologous, more preferably about 70% homologous, even more preferably about 80% homologous, and most preferably about 90% homologous to the desired nucleic acid.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The residues at corresponding positions are then compared and when a position in one sequence is occupied by the same residue as the corresponding position in the other sequence, then the molecules are identical at that position. The percent identity between two sequences, therefore, is a function of the number of identical positions shared by two sequences (i.e., % identity=# of identical positions/total # of positions×100). The percent identity between the two sequences is a function of the number of identical positions shared by the sequences, taking into account the number of gaps, and the length of each gap, which are introduced for optimal alignment of the two sequences.

The comparison of sequences and determination of percent identity between two sequences can be accomplished using a mathematical algorithm. A non-limiting example of a mathematical algorithm utilized for comparison of sequences is the algorithm of Karlin S and Altschul S F, Proc. Natl. Acad. Sci. USA 87:2264-68 (1990), modified as in Karlin S and Altschul S F, Proc. Natl. Acad. Sci. USA 90:5873-77 (1993). Such an algorithm is incorporated into the NBLAST and XBLAST programs (version 2.0) of Altschul S F et al., J. Mol. Biol. 215:403-10 (1990). BLAST nucleotide searches can be performed with the NBLAST program score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul S F et al., Nucleic Acids Res. 25:3389-3402 (1997). When utilizing BLAST and Gapped BLAST programs, the default parameters of the respective programs (e.g., XBLAST and NBLAST) can be used. Another preferred, non-limiting algorithm utilized for the comparison of sequences is the algorithm of Myers E W and Miller W, Comput. Appl. Biosci. 4:11-17 (1988). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Another non-limiting example of a mathematical algorithm utilized for the alignment of protein sequences is the Lipman-Pearson algorithm (Lipman D J and Pearson W R, Science 227:143541 (1985)). When using the Lipman-Pearson algorithm, a PAM250 weight residue table, a gap length penalty of 12, a gap penalty of 4, and a Kutple of 2 can be used. A preferred, non-limiting example of a mathematical algorithm utilized for the alignment of nucleic acid sequences is the Wilbur-Lipman algorithm (Wilbur W J and Lipman D J, Proc. Natl. Acad. Sci. USA 80:726-30 (1983)). When using the Wilbur-Lipman algorithm, a window of 20, gap penalty of 3, Ktuple of 3 can be used. Both the Lipman-Pearson algorithm and the Wilbur-Lipman algorithm are incorporated, for example, into the MEGALIGN program (e.g., version 3.1.7) which is part of the DNASTAR sequence analysis software package.

Additional algorithms for sequence analysis are known in the art, and include ADVANCE and ADAM, described in Torelli A and Robotti C A, Comput. Appl. Biosci. 10:3-5 (1994); and FASTA, described in Pearson W R and Lipman D J, Proc. Natl. Acad. Sci. USA 85:2444-48 (1988).

In a preferred embodiment, the percent identity between two amino acid sequences is determined using the GAP program in the GCG software package, using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6.

Protein alignments can also be made using the Geneworks global protein alignment program (e.g., version 2.5.1) with the cost to open gap set at 5, the cost to lengthen gap set at 5, the minimum diagonal length set at 4, the maximum diagonal offset set at 130, the consensus cutoff set at 50% and utilizing the Pam 250 matrix.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul S F et al., J. Mol. Biol. 215:403-10 (1990). BLAST nucleotide searches can be performed with the NBLAST program, score=100, wordlength=12. to obtain nucleotide sequences homologous to chimeric CCR2B. BLAST protein searches can be performed with the XBLAST program, score=50, wordlength=3 to obtain amino acid sequences homologous to chimeric CCR2B. To obtain gapped alignments for comparison purposes, Gapped BLAST can be utilized as described in Altschul S F et al., Nucleic Acids Res. 25:3389-3402 (1997). When utilizing BLAST and Gapped BLAST programs, the default parameters of the respective programs (e.g., XBLAST and NBLAST) can be used. For example, the nucleotide sequences of the invention can be analyzed using the default Blastn matrix 1-3 with gap penalties set at: existence 11 and extension 1. The amino acid sequences of the invention can be analyzed using the default settings: the Blosum62 matrix with gap penalties set at existence 11 and extension 1.

A "host cell" is intended to include any individual cell or cell culture which can be or has been a recipient for vectors or for the incorporation of exogenous nucleic acid molecules, polynucleotides, and/or proteins. It also is intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, e.g., murine, rat, simian, or human cells.

"Hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". The stringency of a hybridization reaction includes the difficulty with which any two nucleic acid molecules will hybridize to one another. Under stringent conditions, nucleic acid molecules at least 65%, 70%, 75% or more identical to each other remain hybridized to each other, whereas molecules with low percent identity cannot remain hybridized. A preferred, non-limiting example of highly stringent hybridization conditions are hybridization in 6× sodium chloride/sodium citrate (SSC) at about 45° C., followed by one or more washes in 0.2×SSC, 0.1% SDS at 50° C., preferably at 55° C., more preferably at 60° C., and even more preferably at 65 ° C.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide if hybridization can occur between one of the strands of the first polynucleotide and the second. "Complementarity" or homology is quantifiable in terms of the proportion of bases in opposing strands that are expected to hydrogen bond with each other, according to generally accepted base-pairing rules. A polynucleotide which is fully complementary is one in which there are no mismatched DNA basepairs between the first nucleotide sequence and its complement.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes, for example, a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "operably linked" means that a nucleic acid molecule, i.e., DNA, and one or more regulatory sequences (e.g., a promoter or portion thereof) are connected in such a way as to permit transcription of mRNA from the nucleic acid molecule or permit expression of the product (i.e., a polypeptide) of the nucleic acid molecule when the appropriate molecules are bound to the regulatory sequences. Within a fusion construct, the term "operably linked" is intended to indicate that a human CCR2B polynucleotide and a non-human CCR2B polynucleotide are fused in-frame to each other.

As used herein, the terms "polynucleotide" and "oligonucleotides" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

It is contemplated that where the nucleic acid molecule is RNA, the T (thymine) in non-RNA sequences provided herein is substituted with U (uracil). For example, SEQ ID NO:1 is disclosed herein as a DNA sequence. Thus, one of ordinary skill in the art would recognize that an RNA molecule of SEQ ID NO:1, for example, would have T substituted with U.

The term "polypeptide" includes a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

A "primer" includes a short polynucleotide, generally with a free 3'-OH group that binds to a target or "template" present in a sample of interest by hybridizing with the target, and thereafter promoting polymerization of a polynucleotide complementary to the target. A "polymerase chain reaction" ("PCR") is a reaction in which replicate copies are made of a target polynucleotide using a "pair of primers" or "set of primers" consisting of an "upstream" and a "downstream" primer, and a catalyst of polymerization, such as a DNA polymerase, and typically a thermally-stable polymerase enzyme. Methods for PCR are well known in the art, and are taught, for example, in MacPherson M et al., PCR: A Practical Approach, IRL Press at Oxford University Press (1991). All processes of producing replicate copies of a polynucleotide, such as PCR or gene cloning, are collectively referred to herein as "replication". A primer can also be used as a probe in hybridization reactions, such as Southern or Northern blot analyses (see, e.g., Sambrook, J., Fritsh, E. F., and Maniatis, T. Molecular Cloning: A Laboratory Manual, 2nd ed., Cold Spring Harbor Laboratory, Cold Spring Harbor Laboratory Press, Cold Spring Harbor, N.Y., 1989).

A "probe" when used in the context of polynucleotide manipulation includes an oligonucleotide that is provided as a reagent to detect a target present in a sample of interest by hybridizing with the target. Usually, a probe will comprise a label or a means by which a label can be attached, either before or subsequent to the hybridization reaction. Suitable labels include, but are not limited to, radioisotopes, fluorochromes, chemiluminescent compounds, dyes, and proteins, including enzymes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined, for example, by mapping with nuclease S1), as well as protein binding domains (consensus sequences) responsible for the binding of RNA polymerase.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure; and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including, for example, centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

As used herein, a "wild-type" nucleic acid molecule refers to an RNA or DNA molecule having a nucleotide sequence that occurs in nature (e.g., encodes a natural protein).

II. Isolated Polynucleotides Encoding Chimeric CCR2B or Portions thereof

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent because they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a chimeric CCR2B polypeptide (or a portion thereof) can be used to derive the chimeric CCR2B amino acid sequence, using the genetic code to translate the DNA or RNA molecule into an amino acid sequence. Likewise, for any chimeric CCR2B amino acid sequence, corresponding polynucleotide sequences that can encode chimeric CCR2B protein can be deduced from the genetic code (which, because of its redundancy, will produce multiple polynucleotide sequences for any given amino acid sequence). Thus, description and/or disclosure herein of a chimeric CCR2B polynucleotide sequence should be considered to also include description and/or disclosure of the amino acid sequence encoded by the polynucleotide sequence. Similarly, description and/or disclosure of a chimeric CCR2B amino acid sequence herein should be considered to also include description and/or disclosure of all possible polynucleotide sequences that can encode the amino acid sequence. It will be understood that, in discussing the uses of chimeric CCR2B nucleic acid molecules, fragments of such polynucleotides as well as full length chimeric CCR2B polynucleotides can be used.

A chimeric CCR2B polynucleotide can be amplified using cDNA or mRNA as a template and appropriate oligonucleotide primers according to standard PCR amplification techniques. The polynucleotide so amplified can be cloned into an appropriate vector and characterized by DNA sequence analysis. Furthermore, oligonucleotides corresponding to chimeric CCR2B polynucleotide sequences can be prepared by standard synthetic techniques, e.g., using an automated DNA synthesizer.

In a preferred embodiment, an isolated polynucleotide comprises nucleotides 13-1092 of SEQ ID NO:1.

In another preferred embodiment, an isolated polynucleotide comprises a polynucleotide which is a complement of the polynucleotide sequence shown in nucleotides 13-1092 of SEQ ID NO:1 or a portion of this polynucleotide sequence. A polynucleotide which is complementary to nucleotides 13-1092 of SEQ ID NO:1 is one which is sufficiently complementary to nucleotides 13-1092 of SEQ ID NO:1, such that it can hybridize to the polynucleotide sequence shown in nucleotides 13-1092 of SEQ ID NO:1, thereby forming a stable duplex. A polynucleotide which is fully complementary to SEQ ID NO:1 is one in which there are no mismatched DNA basepairs between the complement and SEQ ID NO:1.

In still another preferred embodiment, an isolated polynucleotide comprises a polynucleotide sequence which is at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more homologous to the polynucleotide sequence (e.g., to the entire length of the nucleotide sequence) shown in nucleotides 13-1092 of SEQ ID NO:1.

Moreover, a polynucleotide can comprise only a portion of the polynucleotide sequence of nucleotides 13-1092 of SEQ ID NO:1; for example, a fragment which can be used as a probe or primer or a fragment encoding a biologically active portion of a chimeric CCR2B protein. The probe/primer typically comprises a substantially purified oligonucleotide. In one embodiment, the oligonucleotide comprises a region of nucleotide sequence that hybridizes under stringent conditions to at least about 15, preferably about 20 or 25, more preferably about 30, 35, 40, 45, 50, 55, 60, 65, 75, or 100 consecutive polynucleotides of a sense sequence of nucleotides 13-1092 of SEQ ID NO:1. In another embodiment, a polynucleotide comprises a polynucleotide sequence which is at least about 100, 200, 300, or more nucleotides in length and hybridizes under stringent hybridization conditions to a polynucleotide sequence of nucleotides 13-1092 of SEQ ID NO:1 or a complement thereof.

In another embodiment, a polynucleotide comprises at least about 100, 200, 300, or more contiguous nucleotides of nucleotides 13-1092 of SEQ ID NO:1.

A polynucleotide fragment of SEQ ID NO:1 contains at least a portion of the sequence of SEQ ID NO:1 encoding amino acids 1-35 of SEQ ID NO:2 contiguous with at least a portion of the sequence of SEQ ID NO:1 encoding amino acids 36-300 of SEQ ID NO:2, the fragment contains at least a portion of the sequence of SEQ ID NO:1 encoding amino acids 36-300 of SEQ ID NO:2 contiguous with at least a portion of the sequence of SEQ ID NO:1 encoding amino acids 301-360 of SEQ ID NO:2, or the fragment spans all three regions of SEQ ID NO:1 (i.e., a fragment comprising at least one codon encoding amino acids 1-35 of SEQ ID NO:2 contiguous with all codons encoding amino acids 36-300 of SEQ ID NO:2 contiguous with at least one codon encoding amino acids 301-360 of SEQ ID NO:2). By "at least a portion" is meant that the fragment contains at least one codon from a human region of SEQ ID NO:1 with the remainder of the fragment being from the dog region or that the fragment contains at least one codon from the dog region of SEQ ID NO:2 with the remainder being from a human region. In this way, one of ordinary skill in the art can envision, for example, a polypeptide encoding a 15 amino acid fragment of SEQ ID NO:2 comprising sequences of SEQ ID NO:1 such as, for example, nucleotides 115-159, 112-156, 109-153, 106-150, 103-147, 100-144, 97-141, 94-138, 91-135, 88-132, 85-129, 82-126, 79-123, 76-120, 910-954, 907-951, 904-948, 901-945, 898-942, 895-939, 892-936, 889-933, 886-930, 883-927, 880-924, 877-921, 874-918, and 871-915. Larger and smaller fragments are similarly encompassed by the scope of the present disclosure.

Probes based on the chimeric CCR2B polynucleotide sequence can be used to detect transcripts or genomic sequences encoding the same or homologous proteins. In preferred embodiments, the probe further comprises a label group attached thereto, for example, the label group can be a radioisotope, a fluorescent compound, an enzyme, or an enzyme co-factor.

Polynucleotides that differ from nucleotides 13-1092 of SEQ ID NO:1 due to degeneracy of the genetic code, and thus encode the same chimeric CCR2B protein as that encoded by nucleotides 13-1092 of SEQ ID NO:1, are encompassed by the present disclosure. Accordingly, in another embodiment, an isolated polynucleotide has a polynucleotide sequence encoding a protein having an amino acid sequence shown in SEQ ID NO:2.

In another embodiment, an isolated polynucleotide can be identified based on shared nucleotide sequence identity using a mathematical algorithm. Such algorithms are outlined in more detail above (see, e.g., section I).

The skilled artisan will further appreciate that minor changes may be introduced by mutation into polynucleotide sequences, for example, nucleotides 13-1092 of SEQ ID NO:1, thereby leading to changes in the amino acid sequence of the encoded protein, without altering the functional activity of a chimeric CCR2B protein. For example, nucleotide substitutions leading to amino acid substitutions at "non-essential" amino acid residues may be made in nucleotides 13-1092 of SEQ ID NO: 1. A "non-essential" amino acid residue is a residue that can be altered from the sequence of a chimeric CCR2B polynucleotide (e.g., nucleotides 13-1092 of SEQ ID NO:1) without altering the functional activity of a chimeric CCR2B molecule. Exemplary residues which are non-essential and, therefore, amenable to substitution can be identified by one of ordinary skill in the art by performing an amino acid alignment of chimeric CCR2B-related molecules and determining residues that are not conserved. Such residues, because they have not been conserved, are more likely amenable to substitution.

Accordingly, another aspect pertains to polynucleotides encoding chimeric CCR2B proteins that contain changes in amino acid residues that are not essential for a chimeric CCR2B activity. Such chimeric CCR2B proteins differ in amino acid sequence from SEQ ID NO:2 yet retain an inherent chimeric CCR2B activity. An isolated polynucleotide encoding a variant of a chimeric CCR2B protein can be created by introducing one or more nucleotide substitutions, additions, or deletions into nucleotides 13-1092 of SEQ ID NO:1 such that one or more amino acid substitutions, additions, or deletions are introduced into the encoded protein. Mutations can be introduced into nucleotides 13-1092 of SEQ ID NO:1 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a chimeric CCR2B polypeptide is preferably replaced with another amino acid residue from the same side chain family.

Alternatively, in another embodiment, mutations can be introduced randomly along all or part of a chimeric CCR2B coding sequence, such as by saturation mutagenesis, and, following mutagenesis, the resultant chimeric CCR2B mutant proteins can be expressed recombinantly in a host cell and screened for their ability to mediate MCP-1 dependent calcium mobilization, MCP-1 dependent inhibition of cAMP production, or their ability to bind specifically to MCP-1 or other CCR2B ligands. Other assays of CCR2B function are well known to those of ordinary skill in the art.

III. Isolated Chimeric CCR2B Polypeptides and Fragments thereof

Another aspect of the invention pertains to isolated chimeric CCR2B proteins. In one embodiment, chimeric CCR2B proteins are produced by recombinant DNA techniques. Alternative to recombinant expression, a chimeric CCR2B protein or polypeptide can be synthesized chemically using standard peptide synthesis techniques. It will be understood that in discussing the uses of chimeric CCR2B proteins, e.g., as shown in SEQ ID NO:2, that in some embodiments fragments of such proteins that are not full length chimeric CCR2B polypeptides as well as full length chimeric CCR2B proteins can be used.

Preferably, the chimeric CCR2B protein comprises the amino acid sequence encoded by nucleotides 13-1092 of SEQ ID NO:1 or a portion thereof. In another preferred embodiment, the protein comprises the amino acid sequence of SEQ ID NO:2 or a portion thereof. In other embodiments, the protein has at least 86%, 87%, 88%, 89%, 90%, 91%, 92%, 93%, 94%, 95%, 96%, 97%, 98%, or 99% amino acid identity with the amino acid sequence shown in SEQ ID NO:2 or a portion thereof.

Biologically active portions of a chimeric CCR2B protein include peptides comprising amino acid sequences sufficiently homologous to or derived from the amino acid sequence of the chimeric CCR2B protein, which include less amino. acids than the full length chimeric CCR2B proteins, and exhibit at least one activity of a chimeric CCR2B protein such as, for example, mediation of MCP-1 dependent calcium mobilization.

The invention also provides chimeric CCR2B fusion proteins. For example, in one embodiment, the fusion protein is a GST-chimeric CCR2B member fusion protein in which the chimeric CCR2B member sequences are fused to the C-terminus of the GST sequences. In another embodiment, the fusion protein is a chimeric CCR2B-HA fusion protein in which the chimeric CCR2B member nucleotide sequence is inserted in a vector such as pCEP4-HA vector (Herrscher R F et al., Genes Dev. 9:3067-82 (1995)) such that the chimeric CCR2B member sequence is fused in frame to an influenza hemagglutinin epitope tag. Such fusion proteins can facilitate the purification of a recombinant chimeric CCR2B member.

Fusion proteins and peptides produced by recombinant techniques may be secreted and isolated from a mixture of cells and medium containing the protein or peptide. Alternatively, the protein or peptide may be retained cytoplasmically and the cells harvested, lysed, and the protein isolated. A cell culture typically includes host cells, media, and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a chimeric CCR2B fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al., John Wiley & Sons: 1992). Moreover, many expression vectors are commercially available that already encode a fusion moiety (e.g., a GST polypeptide or an HA epitope tag). A chimeric CCR2B-encoding nucleic acid can be cloned into such an expression vector such that the fusion moiety is linked in-frame to the chimeric CCR2B protein.

In one embodiment, the invention pertains to derivatives of chimeric CCR2B which may be formed by modifying at least one amino acid residue of chimeric CCR2B by oxidation, reduction, or other derivatization processes known in the art.

Systematic substitution of one or more amino acids of a chimeric CCR2B amino acid sequence with a D-amino acid of the same type (e.g., D-lysine in place of L-lysine) may be used to generate more stable peptides. In addition, constrained peptides comprising a chimeric CCR2B amino acid sequence or a substantially identical sequence variation may be generated by methods known in the art (Rizo J and Gierasch L M, Ann. Rev. Biochem. 61:387-416 (1992)); for example, by adding internal cysteine residues capable of forming intramolecular disulfide bridges which cyclize the peptide.

The amino acid sequences of chimeric CCR2B polypeptides identified herein will enable those of skill in the art to produce polypeptides corresponding to chimeric CCR2B peptide sequences and sequence variants thereof. Such polypeptides may be produced in prokaryotic or eukaryotic host cells by expression of polynucleotides encoding a chimeric CCR2B peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Gutte B and Merrifield R B, J. Am. Chem. Soc. 91:501-02 (1969); Chaiken I M, CRC Crit. Rev. Biochem. 11:255-301 (1981); Kaiser E T et al., Science 243:187-92 (1989); Merrifield B, Science 232: 341-47 (1986); Kent S B H, Ann. Rev. Biochem. 57:957-89 (1988); Offord, R. E. (1980) Semisynthetic Proteins, Wiley Publishing.

Peptides can be produced as modified peptides, with non-peptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, may be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides may be used therapeutically to treat disease.

Another embodiment is for fragments of chimeric CCR2B. In a preferred embodiment, a fragment of chimeric CCR2B contains at least a portion of the sequence of amino acids 1-35 of SEQ ID NO:2 contiguous with at least a portion of the sequence of amino acids 36-300 of SEQ ID NO:2, the fragment contains at least a portion of the sequence of amino acids 36-300 of SEQ ID NO:2 contiguous at least a portion of the sequence of amino acids 301-360 of SEQ ID NO:2, or the fragment spans all three regions of SEQ ID NO:2 (i.e., a fragment comprising at least one amino acid from amino acids 1-35 of SEQ ID NO:2 contiguous with all amino acids 36-300 of SEQ ID NO:2 contiguous with and at least one amino acid from amino acids 301-360 of SEQ ID NO:2). By "at least a portion" is meant that the fragment contains at least one amino acid from a human region of the chimeric CCR2B protein with the remainder of the fragment being from the dog region or that the fragment contains at least one amino acid from the dog region of the chimeric CCR2B protein with the remainder being from a human region. In this way, one of ordinary skill in the art can envision, for example, 15 amino acid fragments of SEQ ID NO:2 comprising sequences such as, for example, amino acids 35-49, 34-48, 33-47, 32-46, 31-45, 30-44, 29-43, 28-42, 27-41, 26-40, 25-39, 24-38, 23-37, 22-36, 300-314, 299-313, 298-312, 297-311, 296-310, 295-309, 294-308, 293-307, 292-306, 291-305, 290-304, 289-303, 288-302, and 287-301. Larger and smaller fragments are similarly encompassed by the scope of the present disclosure.

IV. Recombinant Expression Vectors and Host Cells

Another aspect of the invention pertains to vectors, preferably expression vectors, containing a nucleic acid encoding a chimeric CCR2B protein (or a portion thereof). The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., chimeric CCR2B proteins, fusion proteins, and the like).

The recombinant expression vectors of the invention can be designed for expression of chimeric CCR2B proteins or protein fragments in prokaryotic or eukaryotic cells. For example, chimeric CCR2B proteins can be expressed in bacterial cells such as E. coli, insect cells (using baculovirus expression vectors), yeast cells, or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase. Typical fusion expression vectors include, for example, pGEX (Pharmacia Biotech Inc; Smith D B and Johnson K S, Gene 67:31-40 (1988)) and pMAL (New England Biolabs, Beverly, Mass.) which fuse glutathione S-transfers (GST) or maltose E binding protein, respectively, to the target recombinant protein.

Examples of suitable inducible non-fusion E. coli expression vectors include pTrc (Amann E et al., Gene 69:301-15 (1988)) and pET 11d (Studier et al., Gene Expression Technology: Methods in Enzymology 185, Academic Press, San Diego, Calif. (1990) pp. 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman S, Gene Expression Technology: Methods in Enzymology 185, Academic Press, San Diego, Calif. (1990) pp. 119-28). Another strategy is to alter the nucleic acid sequence of the nucleic acid to be inserted into an expression vector so that the individual codons for each amino acid are those preferentially utilized in E. coli (Wada K et al., Nucleic Acids Res. 20(Suppl.):2111-18 (1992)). Such alteration of nucleic acid sequences of the invention can be carried out by standard DNA synthesis techniques.

In another embodiment, the chimeric CCR2B expression vector is a yeast expression vector. Examples of vectors for expression in yeast S. cerivisae include pYepSec1 (Baldari C et al., EMBO J. 6:229-34 (1987)), pMFa (Kurjan J and Herskowitz I, Cell 30:933-43 (1982)), pJRY88 (Schultz L D et al., Gene 54:113-23 (1987)), pYES2 (Invitrogen Corporation, San Diego, Calif.), and picZ (Invitrogen Corp, San Diego, Calif.).

Alternatively, chimeric CCR2B proteins or polypeptides can be expressed in insect cells using baculovirus expression vectors. Baculovirus vectors available for expression of proteins in cultured insect cells (e.g., Sf 9 cells) include the pAc series (Smith G E et al., Mol. Cell. Biol. 3:2156-65 (1983)) and the pVL series (Lucklow V A and Summers M D, Virology 170:31-39 (1989)).

In yet another embodiment, a nucleic acid of the invention is expressed in mammalian cells using a mammalian expression vector. Examples of mammalian expression vectors include pCDM8 (Seed B, Nature 329:840-41 (1987)) and pMT2PC (Kaufman R J et al., EMBO J. 6:187-95 (1987)). When used in mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook, J., Fritsh, E. F., and Maniatis, T. Molecular Cloning: A Laboratory Manual, 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic . acid). Tissue-specific regulatory elements are known in the art. Non-limiting examples of suitable tissue-specific promoters include the albumin promoter (liver-specific; Pinkert C A et al., Genes Dev. 1:268-77 (1987)), lymphoid-specific promoters (Calame K and Eaton S, Adv. Immunol. 43:235-75 (1988)), in particular promoters of T cell receptors (Winoto A and Baltimore D, EMBO J. 8:729-33 (1989)) and immunoglobulins (Banerji J et al., Cell 33:729-40 (1983); Queen C and Baltimore D, Cell 33:741-48 (1983)), neuron-specific promoters (e.g., the neurofilament promoter; Byrne G W and Ruddle F H, Proc. Natl. Acad. Sci. USA 86:5473-77 (1989)), pancreas-specific promoters (Edlund T et al., Science 230:912-16 (1985)), and mammary gland-specific promoters (e.g., milk whey promoter; U.S. Pat. No.4,873,316 and EP 0 264 166). Developmentally-regulated promoters are also encompassed, for example the murine hox promoters (Kessel M and Gruss P, Science 249:374-79 (1990)) and the α-fetoprotein promoter (Camper S A and Tilghman S M, Genes Dev. 3:537-46 (1989)).

Moreover, inducible regulatory systems for use in mammalian cells are known in the art, for example systems in which gene expression is regulated by heavy metal ions (see e.g., Mayo K E et al., Cell 29:99-108 (1982); Brinster R L et al., Nature 296:39-42 (1982); Searle P F et al., Mol. Cell. Biol. 5:1480-89 (1985)), heat shock (see e.g., Nouer L et al. (1991) in Heat Shock Response, ed. Nouer L, CRC, Boca Raton, Fla., pp. 167-220), hormones (see e.g., Lee F et al., Nature 294:228-32 (1981); Hynes N E et al., Proc. Natl. Acad. Sci. USA 78:2038-42 (1981); Klock G et al., Nature 329:734-36 (1987); Israel D I and Kaufman R J, Nucleic Acids Res. 17:2589-2604 (1989); WO 93/23431), FK506-related molecules (see e.g., WO 94/18317) or tetracyclines (Gossen M and Bujard H, Proc. Natl. Acad. Sci. USA 89:5547-51 (1992); Gossen M et al., Science 268:1766-69 (1995); WO 94/29442; WO 96/01313). Accordingly, in another embodiment, the invention provides a recombinant expression vector in which a chimeric CCR2B DNA is operably linked to an inducible eukaryotic promoter, thereby allowing for inducible expression of a chimeric CCR2B protein in eukaryotic cells.

Also known in the art are methods for expressing endogenous proteins using one-arm. homologous recombination (see, e.g., U.S. Published Patent Application No. 2005/0003367; Zeh et al., Assay Drug Dev. Technol. 1:755-65 (2003); Qureshi et al., Assay Drug Dev. Technol. 1:767-76 (2003)). Briefly, an isolated genomic construct comprising a promoter operably linked to a chimeric CCR2B targeting sequence is introduced into a homogeneous population of cells (such as, for example, a homogeneous population of a human cell line). The promoter is heterologous to the chimeric CCR2B target gene. Following recombination, the promoter controls transcription of an mRNA that encodes a chimeric CCR2B polypeptide. The population of cells is then incubated under conditions which cause expression of the chimeric CCR2B polypeptide.

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to chimeric CCR2B mRNA. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub H et al., Trends Genet. 1:22-25 (1985).

Another aspect of the invention pertains to host cells into which a recombinant expression vector of the invention has been introduced. For example, a chimeric CCR2B protein can be expressed in bacterial cells (such as, for example, E. coli), insect cells, yeast, or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including, for example, calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual, 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a chimeric CCR2B protein or can be introduced on a separate vector. Cells stably transfected with the introduced nucleic acid can be identified by drug selection (e.g., cells that have incorporated the selectable marker gene will survive, while the other cells die).

The regulation of the expressed gene can be brought about by the double stable expression first of a "regulator" plasmid, which contains the tet-controlled transactivator (tTA) and a second "response" plasmid, which contains chimeric CCR2B, under the control of a promoter sequence that includes the tetracycline response element (TRE). The commercially available regulator plasmids are in vectors engineered for neomycin selection, necessitating that response vectors be constructed to include a second selectable marker. Using such methods, chimeric CCR2B expression can be turned off in the presence of an agent, for example, tetracycline or a tetracycline-related compound (e.g., doxycycline) and turned on when the agent, for example, tetracycline, is not added to the culture medium. Construction of this type of cell line permits the stable expression of chimeric CCR2B in cells in which it is normally toxic.

A host cell of the invention, such as a prokaryotic or eukaryotic host cell in culture, can be used to produce (i.e., express) a chimeric CCR2B protein. Accordingly, the invention further provides methods for producing a chimeric CCR2B protein using the host cells of the invention. In one embodiment, the method comprises culturing the host cell of invention (into which a recombinant expression vector encoding a chimeric CCR2B protein has been introduced) in a suitable medium such that a chimeric CCR2B protein is produced. In another embodiment, the method further comprises isolating a chimeric CCR2B protein from the medium or the host cell.

EXAMPLES

The present invention is further defined in the following Examples. It should be understood that these Examples, while indicating preferred embodiments of the invention, are given by way of illustration only. From the above discussion and these Examples, one skilled in the art can ascertain the preferred features of this invention, and without departing from the spirit and scope thereof, can make various changes and modification of the invention to adapt it to various uses and conditions.

Example 1

The amino acid sequence of the dog-human CCR2B chimeric protein (SEQ ID NO:2) was submitted to Blue Heron Biotech (Bothell, Wash., USA), along with specifications for 5' and 3' modifications to the sequence, including restriction sites (HindIII and EcoRI) for cloning. Blue Heron Biotech applied a primate codon optimization algorithm, resulting in SEQ ID NO:1. This sequence was synthesized and delivered in a pUC-based cloning vector, from which the chimeric CCR2B-encoding insert was subcloned into pcDNA 3.1 (+) digested with HindIII and EcoRI.

Example 2

The chimeric CCR2B/cDNA3.1 plasmid of Example 1 was expressed in CHO-K1 cells using the Lipofectamine-Plus reagent (Invitrogen, Carlsbad, Calif., USA) according to manufacturer's instructions, and the resulting stable cell lines following selection with the antibiotic G418 were assayed for MCP-1-dependent calcium mobilization in a FLIPR assay. Cells were plated at 15,000 per well in a 384-well assay plate one day prior to assay. Calcium-3 indicator dye (Molecular Devices, Sunnyvale, Calif., USA) was added 1 hr prior to assay, and cells were incubated at 37° C. For the agonist assay, human MCP-1 was added to cells, followed immediately by reading of calcium mobilization on the FLIPR. RFU counts (Max-Min) were recorded for each MCP-1 concentration assayed. For the antagonist assay, the antagonist was added to the cells 20 min prior to addition of MCP-1.

The EC50 of this functional interaction was 1.5 nM, a value comparable to the EC50 of 3 nM for MCP-1 signaling in THP-1 cells, a human monocyte cell line with endogenous CCR2B expression (see FIG. 3). The MCP-1-dependent activation of the chimeric dog-human receptor was inhibited with a CCR2 non-competitive antagonist. However, the antagonist compound was considerably less potent in its inhibition of the signaling in dhCCR2B/CHO-K1 cells (IC50 approximately 20 μM) than THP-1 cells (IC50 approximately 300 nM). These results indicate that while the dog residues in the TM and loop domains can functionally substitute for the orthologous human residues in the propagation of hMCP-1 signaling, they differ in their functional interaction with the antagonist compound.

Example 3

Figure 4A:
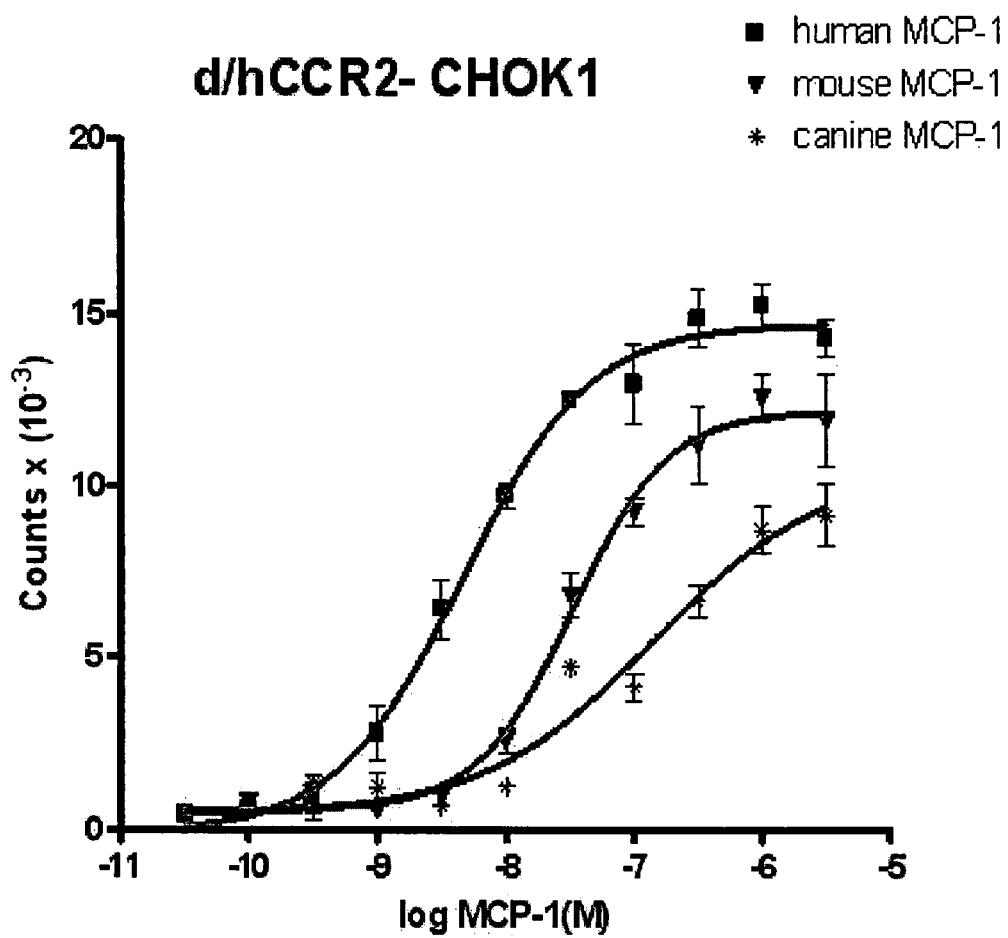
FIG. 4A is a FLIPR assay of calcium mobilization stimulated by human (squares), mouse (triangles), and canine (asterisks) MCP-1 in dog-human chimeric CCR2B-expressing CHOK1 cells. Human MCP1 (4.6 nM)>mouse MCP (38 nM)>cMCP-1 (138 nM).
Figure 4B:
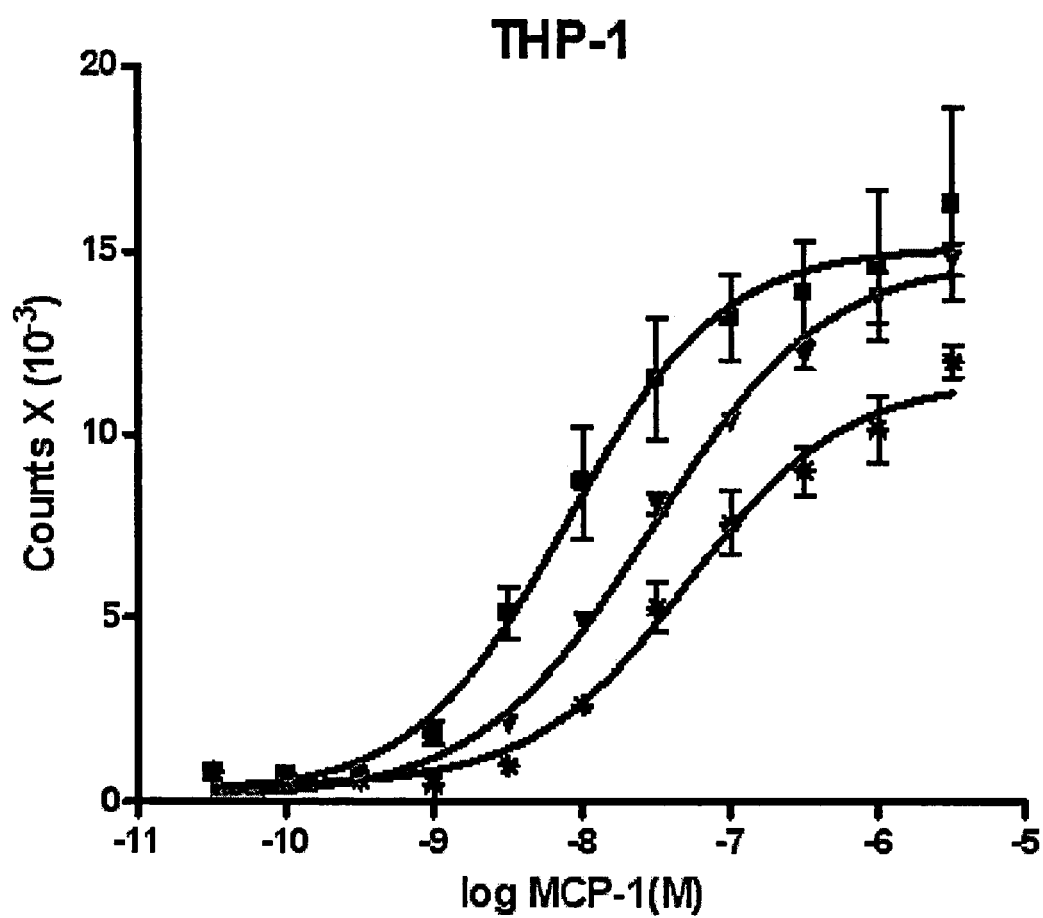
FIG. 4B is a FLIPR assay of calcium mobilization stimulated by human (squares), mouse (triangles), and canine (asterisks) MCP-1 in THP-1 cells, which endogenously express human CCR2B). Human MCP1 (8 nM)>mouse MCP (30 nM)>cMCP-1 (53 nM).

The MCP-1 activation of calcium mobilization in CCR2B/CHOK1 cells of Example 2 was extended to include examination of the effects of mouse and canine MCP-1 (FIG. 4A). Mouse MCP-1 (EC50=38 nM) was less potent than human MCP-1 at activation CCR2 signaling, and canine MCP-1 (EC50=138 nM) was even less potent, despite the greater amino acid identity between human and canine MCP-1 (82%) than between human and mouse MCP-1 (55%). Examination of the same three species of ligand in the calcium mobilization assay in THP-1 cells (FIG. 4B) yielded the result that mouse MCP-1 (EC50=30 nM) and canine MCP-1 (EC50=53 nM) were less potent than human MCP-1. The qualitative similarity of the results in the CHOK1 cells expressing the chimeric receptor and THP-1 cells, with their endogenous expression of the human receptor, lends evidence that the chimeric receptor faithfully recapitulates the activation pharmacology of the native receptor.

What is claimed is:

1. An isolated polynucleotide comprising a nucleotide sequence selected from the group consisting of:
    (a) a nucleotide sequence encoding a chimeric CCR2B polypeptide having at least 95% identity with the amino acid sequence set forth in SEQ ID NO:2, said chimeric CCR2B polypeptide having the ability to mediate Monocyte chemoattractant protein-1 (MCP-1) dependent calcium mobilization; and
    (b) a nucleotide sequence complementary to (a).

2. The isolated polynucleotide of claim 1, wherein the nucleotide sequence of (a) encodes the amino acid sequence set forth in SEQ ID NO:2.

3. The isolated polynucleotide of claim 2, wherein the nucleotide sequence of (a) is nucleotides 13-1092 of SEQ ID NO:1.

4. A vector comprising the isolated polynucleotide of claim 1.

5. A transformed host cell comprising the isolated polynucleotide of claim 1.

6. The transformed host cell of claim 5, wherein the transformed host cell is a bacterial cell, a yeast cell, an insect cell, or a mammalian cell.

7. A method of producing a chimeric CCR2B polypeptide comprising
    (a) culturing a transformed host cell of claim 5 such that a chimeric CCR2B polypeptide is produced; and
    (b) optionally recovering the chimeric CCR2B polypeptide of step (a).

* * * * *

SEQUENCE LISTING

```
<160> NUMBER OF SEQ ID NOS: 2

<210> SEQ ID NO 1
<211> LENGTH: 1099
<212> TYPE: DNA
<213> ORGANISM: Artificial
<220> FEATURE:
<223> OTHER INFORMATION: Dog/human CCR2B chimera

<400> SEQUENCE: 1
aagcttgcca ccatgctgag cacgtcacgc tcacgcttta ttagaaacac caatgagagc      60
ggggaagagg tgacgacttt ctttgattac gactacgggg cgccttgcca caagtttagt     120
gtgcgacagg tggctgctgg tttgctgccg cctctgtaca gtcttgtctt tattttcggg     180
tttgtgggaa acatgcttgt tgtgctgatt ttgatcaact gtaagaagct gaagtccatg     240
accgacatat atctgctgaa ccttgctatt tccgatttgc ttttctcct gacgatccct      300 ttttgggccc actatgccgc taacggctgg ctgctgggcg aagttatgtg caagtccttc     360
accggcctct atcacatagg gtactttgga gggacgtttt tcattatact gcttactatt     420
```

```
gatcgatatc tggcaatagt ccacgccgtc ttcgcgttga aggcccggac cgtcacattc      480
ggagtggtta cttccggggt tacatggatg gttgcagtgt tcgcctctct cccccgaatc      540
atattcacca ctgtccagat cgaagattct ttctcttctt gtagcccaca atttcagcag      600
gcctggaaga acttccatac gattatgcgg agcgtgttgg gcctggtcct gccacttttg      660
gtcatggtga tttgttacag cgccattctg aagaccctgc tgagatgtcg gaacgagaaa      720
aagagacata aggccgtgaa gctgatcttc gtgatcatga tcgtctattt tttgttttgg      780
gctcctaaca acattgtgct gctcctgagt accttccagg agagcttcaa tgtatccaac      840
tgtaagtcaa cctctcagct tgaccagatt atgcaagtga cggagactct gggaatgacc      900
cactgctgtg tgaacccgat tatctacgca ttcgtcgggg aaaaattcag aagatacctg      960
tctgtattct tcggaagcat cattactaag cgattctgta acagtgccc ggtcttttac      1020 agggagaccg tagacggagt taccagcacc aatacccta gcacggggga gcaagaagtt      1080
tccgccgggc tgtgaattc                                                  1099
```

<210> SEQ ID NO 2
<211> LENGTH: 360
<212> TYPE: PRT
<213> ORGANISM: Artificial
<220> FEATURE:
<223> OTHER INFORMATION: Dog/human CCR2B chimera

<400> SEQUENCE: 2

```
Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Ser Val Arg Gln Val Ala Ala Gly Leu Leu Pro Pro Leu
            35                  40                  45

Tyr Ser Leu Val Phe Ile Phe Gly Phe Val Gly Asn Met Leu Val Val
        50                  55                  60

Leu Ile Leu Ile Asn Cys Lys Lys Leu Lys Ser Met Thr Asp Ile Tyr
65                  70                  75                  80

Leu Leu Asn Leu Ala Ile Ser Asp Leu Leu Phe Leu Leu Thr Ile Pro
                85                  90                  95

Phe Trp Ala His Tyr Ala Ala Asn Gly Trp Leu Leu Gly Glu Val Met
            100                 105                 110

Cys Lys Ser Phe Thr Gly Leu Tyr His Ile Gly Tyr Phe Gly Gly Thr
        115                 120                 125

Phe Phe Ile Ile Leu Leu Thr Ile Asp Arg Tyr Leu Ala Ile Val His
    130                 135                 140

Ala Val Phe Ala Leu Lys Ala Arg Thr Val Thr Phe Gly Val Val Thr
145                 150                 155                 160

Ser Gly Val Thr Trp Met Val Ala Val Phe Ala Ser Leu Pro Arg Ile
                165                 170                 175

Ile Phe Thr Thr Val Gln Ile Glu Asp Ser Phe Ser Ser Cys Ser Pro
            180                 185                 190

Gln Phe Gln Gln Ala Trp Lys Asn Phe His Thr Ile Met Arg Ser Val
        195                 200                 205

Leu Gly Leu Val Leu Pro Leu Leu Val Met Val Ile Cys Tyr Ser Ala
    210                 215                 220

Ile Leu Lys Thr Leu Leu Arg Cys Arg Asn Glu Lys Lys Arg His Lys
225                 230                 235                 240
```

-continued

```
Ala Val Lys Leu Ile Phe Val Ile Met Ile Val Tyr Phe Leu Phe Trp
            245             250             255

Ala Pro Asn Asn Ile Val Leu Leu Leu Ser Thr Phe Gln Glu Ser Phe
            260             265             270

Asn Val Ser Asn Cys Lys Ser Thr Ser Gln Leu Asp Gln Ile Met Gln
        275             280             285

Val Thr Glu Thr Leu Gly Met Thr His Cys Cys Val Asn Pro Ile Ile
    290             295             300

Tyr Ala Phe Val Gly Glu Lys Phe Arg Arg Tyr Leu Ser Val Phe Phe
305             310             315             320

Arg Lys His Ile Thr Lys Arg Phe Cys Lys Gln Cys Pro Val Phe Tyr
            325             330             335

Arg Glu Thr Val Asp Gly Val Thr Ser Thr Asn Thr Pro Ser Thr Gly
            340             345             350

Glu Gln Glu Val Ser Ala Gly Leu
        355             360
```